United States Patent [19]

Masri et al.

[11] 4,167,447

[45] Sep. 11, 1979

[54] METHOD FOR INSOLUBILIZING ENZYMES ON CHITOSAN

[75] Inventors: Merle S. Masri, Emeryville; Virginia G. Randall; William L. Stanley, both of El Cerrito, all of Calif.

[73] United States of America as represented by the Secretary of Agriculture, Washington, D.C.

[21] Appl. No.: 889,672

[22] Filed: Mar. 24, 1978

Related U.S. Application Data

[63] Continuation-in-part of Ser. No. 706,980, Jul. 19, 1976, Pat. No. 4,089,746.

[51] Int. Cl.$^2$ .................................................. C07G 7/02
[52] U.S. Cl. ....................................................... 435/178
[58] Field of Search .................... 195/63, 68, DIG. 11

[56] References Cited

U.S. PATENT DOCUMENTS

| | | | |
|---|---|---|---|
| 3,909,358 | 9/1975 | Stanley et al. | 195/63 |
| 4,094,743 | 6/1978 | Leuba | 195/63 |

*Primary Examiner*—Lionel M. Shapiro
*Attorney, Agent, or Firm*—M. Howard Silverstein; David G. McConnell; Theodore J. Leitereg

[57] ABSTRACT

Insolubilized but active enzymes are prepared in a variety of ways. In one embodiment of the invention an aqueous solution of an enzyme is mixed with chitosan dissolved in water at pH 3–7 and an insolubilized product is precipitated therefrom by addition of alkali or a source of sulfate ions. Another embodiment of the invention involves contacting solid chitosan sulfate with an aqueous solution of the enzyme to be immobilized. In yet another embodiment of the invention solid chitosan is cross-linked with a polyfunctional cross-linking agent and then contacted with an aqueous solution of an enzyme. Enzymes insolubilized in accordance with the invention retain a substantial part of their original activity.

9 Claims, No Drawings

METHOD FOR INSOLUBILIZING ENZYMES ON CHITOSAN

CROSS-REFERENCE TO RELATED APPLICATION

This is a continuation-in-part of U.S. Patent Application Ser. No. 706,980, filed July 19, 1976 now U.S. Pat. No. 4,089,746.

BACKGROUND OF THE INVENTION

1. Field of the Invention

This invention relates to and has among its objects the provision of novel water-insoluble but active enzyme products and methods for preparing them. Further objects of the invention will be evident from the following description wherein parts and percentages are by weight unless otherwise specified.

2. Description of the Prior Art

In recent years there has been considerable interest in preparing enzymes in insolubilized (sometimes referred to as immobilized) form. Such products enable enzyme catalyzed reactions to be carried out in a simplified and efficient manner. Typically, the insolubilized enzyme is placed in a cylindrical vessel and a solution of the substrate to be reacted is passed through the enzyme column. The reaction takes place within the column and the effluent liquor contains the reaction products. With this system the enzyme can be used repeatedly for processing fresh batches of the substrate. Various techniques have been advocated for preparing insolubilized enzymes. One procedure is to entrap the enzyme in polymerizing polyacrylamide; another is to absorb it on insoluble media such as ion exchange resins, alumina, etc.

SUMMARY OF THE INVENTION

One particular method for immobilizing enzymes on chitosan is described in the aforementioned U.S. Patent Application, which is incorporated herein by reference. Insolubilized enzymes are prepared by mixing an aqueous solution of an enzyme with an aqueous solution of chitosan and then adding a polyfunctional cross-linking agent to form a gel. The so-produced gel is reacted with a reducing agent to form a granular insolubilized enzyme, which has a substantial part of its original activity.

In accordance with the instant invention insolubilized enzymes are prepared from enzymes which are in a normal or native (soluble) state in three distinct ways, all involving immobilization on chitosan. In one embodiment of the invention, an enzyme is dissolved in water and mixed with a solution of chitosan in water at pH 3-7. An insolubilized product is precipitated from the mixture by addition of either alkali or a source of sulfate ions. Another variation of the present invention involves a procedure wherein solid chitosan sulfate is prepared and treated with a solution of an enzyme in water. The resulting insolubilized enzyme product is ready for use. In yet another embodiment of the instant invention, solid chitosan is partially cross-linked with a polyfunctional cross-linking agent. Then, the so-treated chitosan is mixed with an aqueous solution of an enzyme to yield an immobilized enzyme product.

A primary advantage of the products of the invention is that their activity is retained over long periods of use. Thus, the products of the invention have the advantage not only of being reusable, but also usable under conditions of continuous operations for long periods of time and with large amounts of substrates.

Another advantage of the product of the invention is that it has a granular texture. Consequently, the instant product acts as its own carrier or support so that it can be formed into a column through which water and other liquids can percolate readily. This is in sharp contrast to known insolubilized enzymes which are generally amorphous materials that cannot be used directly in a column because liquids will not flow therethrough. These known products require the addition of a carrier such as diatomaceous earth, crushed firebrick, or the like to provide a liquid-permeable mass.

Another advantage of the invention is that the products are afforded by simple procedures using readily-available reactants. No exotic chemicals or complicated procedures are required. Nonetheless, the products retain a significant and sufficient part of the activity of the starting enzyme. In some cases the major part of the original activity is retained.

A further advantage of the invention is that useful products can be prepared from any enzyme source, including pure enzymes, enzyme concentrates, crude enzyme preparations, and even such substances as animal organs, plant parts, microbial cultures, and the like. Important in this regard is that application of the herein-described reactants causes most of the active enzyme to be selectively precipitated even where it is present in minute quantity, e.g., as little as 1 mg. of active enzyme in association with gram quantities of inactive components. Accordingly, the invention provides the means for preparing insolubilized products from enzymes which previously were difficult to insolubilize or which were never insolubilized.

Another advantage of the invention lies in the precise control that one can exercise over the extent and direction of enzymic reactions. This results because of the solid nature of the products of the invention which allows specific amounts to be metered out to suit any particular situation.

Another advantage of the invention is that external forces, such as heat, acid, and the like, which might be detrimental to the enzyme, need not be applied to stop the reaction. It is only necessary to separate the granular product from the solution in order to short-stop the reaction.

A further advantage of the invention is explained as follows: Most enzymes have an optimum pH, that is, a pH value at which the enzyme exhibits maximum activity. We have found that insolubilizing an enzyme in accordance with the invention produces a shift in this optimum pH, generally to a lower value. This particular aspect of the invention is quite important where an acidic food product (e.g., a fruit juice) is to be treated enzymatically, since it yields efficient results with enzymes which normally would operate inefficiently at the low pH provided by the acidic food.

DESCRIPTION OF THE PREFERRED EMBODIMENTS

The term "dispersion" used herein includes dispersions, solutions, emulsions, suspensions, mixtures, and the like.

In accordance with one embodiment of the invention, the enzyme to be insolubilized is dissolved in distilled water. When necessary the pH of the water is adjusted by conventional methods such as adding an acid, buffer, etc., to a level at which the enzyme is soluble. Appropriate pH's to use with any particular enzyme are described in the literature. In many cases a pH of about 3 to 7 employed. It may further be noted that oftentimes the starting material already contains a buffer or other pH adjusting agent so that when it is mixed with water the resulting dispersion will exhibit a pH at which the enzyme is most soluble. This is particularly the case with commercially available enzyme preparations. It is obvious that in such cases there is no need to apply any pH adjustment.

Following preparation of the aqueous solution of the starting material, a mechanical separation step such as filtration or decantation can be applied to remove fillers, debris, or other undissolved material.

Next, chitosan is dissolved in water containing a small amount of acid to effect solution of the chitosan. The amount of acid is generally that necessary to adjust the pH of the dispersion to about from 3 to 7. Usually, this amount is about 4 to 5 milliequivalents of acid per gram of chitosan. As the acid one may use hydrochloric acid, phosphoric acid, acetic acid, citric acid, and the like. Furthermore, one may employ a buffer to attain the desired pH level and effect solubilization of the chitosan. It should be noted, however, that an acid which forms an insoluble precipitate with chitosan, such as, for example, sulfuric acid, cannot be used in the process of the invention.

Chitosan is a polyamino polysaccharide obtained by N-deacetylation of chitin with strong alkali and heat. Chitin is a polysaccharide wherein the primary repeating unit in the molecule is 2-deoxy-2-(acetylamino)-glucose. In general, about one out of every six units in chitin is not acetylated, whereas in chitosan essentially all the repeating units are not acetylated. It should be noted that the extent of nonacetylation can be controlled by the severity of the deacetylation reaction.

Chitin is readily prepared by removing the impurities from shells of crab, shrimp, lobsters, crayfish, and the like, which are abundantly available from seafood processing plants, and for exoskeletons of insects.

Next, the aqueous dispersion of starting enzyme is mixed with the aqueous dispersion of chitosan. Generally, about 10 to 100 milligrams of crude enzyme per gram of dry chitosan are used. The mixture is agitated gently by conventional means such as shaking, stirring, or the like, while being held for approximately 5-20 minutes at a temperature of about from 10 to 25° C.

It should be mentioned that the enzyme and the chitosan can be simultaneously dissolved in water at the proper pH to produce the above mixture directly.

Next, the mixture is treated to precipitate an insolubilized enzyme product therefrom. Accordingly, alkali may be added for this purpose. Thus, one may add, for example, sodium or potassium hydroxide, ammonia, sodium or potassium carbonate, sodium or potassium bicarbonate, and so forth, to precipitate an insolubilized enzyme product, which is collected by filtration and washed several times with distilled water to remove excess reagents. The so-prepared insolubilized enzyme is ready for use. Usually, about 4-5 milliequivalents of alkali are required per gram of chitosan.

Alternatively, a source of sulfate ions may be added to the above mixture of solubilized enzyme and chitosan to obtain an enzyme immobilized on chitosan sulfate. For example, one may add sodium sulfate, potassium sulfate, ammonium sulfate, or the like, to the mixture of solubilized chitosan and enzyme. In addition, sulfric acid may be employed as the precipitating agent. Other sources of sulfate ions will be suggested to those skilled in the art from an understanding of the principles of the invention. Approximately 2-3 millimoles of sulfate ions are used per gram of chitosan.

In another embodiment of the invention solid chitosan sulfate is prepared as a preliminary step. Thus, chitosan may be divided into small pieces of about 10-60 mesh, such as flakes, by conventional techniques and contacted with sulfuric acid to produce chitosan sulfate. On the other hand, chitosan can be solubilized as described above and chitosan sulfate precipitated from the solution by addition thereto of a source of sulfate ions such as those listed hereinabove. Generally, the amount of sulfate ions used is about 2-5 millimoles per gram of chitosan. The so-prepared chitosan sulfate is washed with water to remove excess sulfate ions prior to application of the next step in this embodiment of the invention.

The solid chitosan sulfate is contacted with an aqueous solution of an enzyme. Usually, about 0.01-0.10 parts of crude enzyme per part of chitosan sulfate are used. The mixture is gently agitated by conventional means such as shaking, stirring, or the like, while being held for 5-20 minutes at a temperature of about 10°-25° C. The product is collected by filtration and washed several times with distilled water to remove excess reagents.

A particular example of the aforementioned embodiment of the invention follows. Chitosan sulfate is dissolved in boiling water and the solution is allowed to cool. At a temperature of approximately 50° C. chitosan sulfate begins to precipitate. At this point a solution of the enzyme to be insolubilized is mixed with the above solution. The resultant mixture is immediately chilled on ice to facilitate formation of an immobilized enzyme product and to avoid heat denaturation of the enzyme. The product is collected and washed as described above.

In another embodiment of the method of the invention, pieces of chitsoan of 10-60 mesh are suspended in water. To this suspension is added a polyfunctional cross-linking agent, i.e., one with more than one functional moiety, such as a di- or polyaldehyde, a di- or polyisocyanate, a di- or polyacid chloride, and the like. The amount of polyfunctional cross-linking agent depends on the nature of the enzyme to be treated; generally, 0.5 to 3 millimoles thereof per gram of chitosan may be used. The resulting cross-linked chitosan is washed with water to remove any excess cross-linking agent and then mixed with an aqueous solution of the enzyme to be immobilized; about 0.01-0.10 parts of dissolved enzyme per part of chitosan are employed. The mixture is agitated gently for a period of about 5 to 20 minutes. In general, the temperature of the reaction should be about 10 to 25° C., preferably ambient temperature. The product is collected by filtration and washed several times with distilled water or other suitable solvent to remove excess reagents prior to its use.

The polyfunctional cross-linking agent must contain more than one functional group. For example, one may employ a polyaldehyde, i.e., a compound containing more than one aldehyde function, such as glyoxal, glutaraldehyde, dialdehyde starch (DAS), succinaldehyde, malonaldehyde, adipaldehyde, pimelaldehyde, formaldehyde which has been hydrated in water, and the like. As the polyisocyanate, one may employ cyclohexyl diisocyanate, 4,4'-dicyclohexylmethane diisocyanate, hexamethylene diisocyanate, dimer oleic acid diisocyanate, 1-isocyanato-3,3,5-trimethyl5-isocyanatomethylcyclohexane, N-(1,1-dimethyl-3-oxobutyl) acrylamide and its hydroxy-methylated derivative, hexadecane diisocyanate, etc. Other polyfunctional cross-linking agents will be suggested to those skilled in the art from an understanding of the description of the instant process.

Usually, the starting enzyme contains inactive proteins and it is desirable to remove these from the final product. To this end the insolubilized enzyme is washed with distilled water for a long period, e.g., about 60 minutes. It is then soaked sequentially in (a) several volumes of 10–50% aqueous sodium chloride, (b) a potassium acetate buffer at pH 7, and, finally, (c) a potassium acetate buffer at a pH whereat the enzyme product is collected by filtration and is ready for use.

The invention is of wide versatility and can be applied to enzymes of all kinds, individually or in combination, illustrative examples being alcohol dehydrogenase, amino acid oxidase, $\alpha$- and $\beta$-amylases, arginase, asparaginase, catalase, cellulase, chymotrypsin, collagenase, deoxyribonuclease, diaphorase, elastin, emulsin, ficin, glucose oxidase, histidase, hyaluronidase, invertase, lactase, peroxidase, phosphatases, lipase, lipoxidase, lysozyme, papain, chymopapain, pepsin, pectin methyl esterase, polyphenol oxidase, rennin, ribonuclease, trypsin, tyrosinase, urease, etc. The starting enzyme need not be a purified substance but may be a preparation containing an enzyme. Thus, for example, one may employ microbial preparations which contain enzymes, typically, cultures or cells of yeasts, molds, bacteria, and the like. Other enzyme-containing preparations which may be applied to the process of the invention are such materials as animal organs, e.g., pancreas, liver, etc., insects and insect parts, barley malt, pineapple, papaya, etc.

The products of the invention can be utilized in a variety of ways. A few examples are provided below by way of illustration and not limitation. Whey, currently a waste material in the production of cheese, can be converted efficiently to glucose and galactose, which are useful as fermentation media and the like, by contacting the watery whey with an insolubilized lactase product prepared in accordance with the invention. An insolubilized protease enzyme can be employed to prevent turbidity in beer, wine, fruit juices, etc. Other applications include hydrolyzing starch to glucose, inverting sucrose solutions for the manufacture of candy, conversion of glucose to fructose, de-glucosing egg whites, conversion of dilute alcohol solutions to vinegar, etc.

EXAMPLES

The invention is demonstrated further by the following illustrative examples.

Chitosan was secured from Food Chemical Company of Seattle, Washington. The sample was ground in a Wiley mill to pass 1 mm screen and was sieved further to various mesh sizes. The major fraction, 30–40 mesh size, was used in the experiments outlined below. The product had a moisture content of about 9% and titrated about 4.5 milliequivalents of hydrogen ion/g to a pH of about 4.2

Lactose was a crude acid tolerant $\beta$-galactosidase from Aspergillus niger and was obtained from Wallerstein Company of Morton Grove, Ill., as lactase LP; the product hydrolyzed 10 micromoles lactose/min./mg of crude enzyme at 40° C. in potassium acetate buffer pH 4.

Invertase was standardized liquid "Sucrovert" preparation derived from yeast and was obtained from SuCrest Corporation (New York, N.Y.). The solution hydrolyzed 6.7 mmole sucrose/min./ml at 40° C. at pH 5.

Lactase activity was measured on a shaker water bath at 40° C. with 0.4 M lactose solution in 0.1 M potassium acetate buffer, pH 4.0 as substrate; usually about 0.2–1.0 g of the chitosan products were used in 25 ml of substrate solution and filtered 1 ml aliquots were withdrawn at different time intervals to determine the rate of glucose production during incubation. Glucose was measured by the glucose oxidasechromogen procedure supplied by Worthington Biochemical Corporation (Freehold, N.J.) as Glucostat. Clinistix reagent strips (Miles Laboratory, Elkhart, Ind.) were also used for semi-quantitative measurement of glucose in exploratory tests.

Invertase activity of products was measured from the rate of glucose formation in the bath incubation mixture in a similar way at 40° C. with 0.1 M sucrose in 0.1 M phosphate buffer pH 5.0 as substrate.

EXAMPLE 1

Run 1: A solution of 1 g of dry chitosan in 50 ml of water containing 4 ml of 1 N HCl was prepared. To this solution was added a solution of 0.1 g of crude lactase in 10 ml of water. The mixture was swirled for 10 minutes. Then, 40 ml of a dilute 0.1 N sodium hydroxide solution was added slowly to the mixture with vigorous stirring.

The product (CHT-LA) was separated from the reaction mixture by filtration and washed with distilled water, followed by 0.5 M phosphate buffer (potassium di-hydrogen phosphate and disodium hydrogen phosphate mixture) of pH 7.0, then with phosphate buffer of pH 5.6, and finally with distilled water.

Run 2: The procedure outlined above in Run 1 was followed to prepare a mixture contaning lactase and chitosan. Next, 20 ml of 0.1 M aqueous sodium sulfate was slowly added to the mixture, with stirring. The product (CHT-SO$_4$-LA) was separated by filtration and treated as described in Run 1.

Run 3: A solution of 15.5 g of dry chitosan in 600 ml of water containing 75 ml of 1 N HCl was prepared. To this solution was added 75 ml of 0.5 M aqueous sodium sulfate. The precipitate was collected by decantation and filtration, washed with water, methanol, and ether, and dried in air (17.2 g).

A sample (0.4 g) of the above product was dissolved in 40 ml of boiling water. The solution was cooled to about 50° C. at which point chitosan sulfate began to precipitate. To this mixture was added 30 mg of crude lactase 1 ml of water with stirring. The mixture was immediately placed on ice. The immobilized enzyme (CHT-SO$_4$-LA) was collected and washed a described above in Run 1.

The lactase activities of CHT-LA, CHT-SO$_4$-LA (Run 2), and CHT-SO$_4$-Run 3) were determined by the Clinistix reagent strip method; all three insolubilized products were enzymatically active. The active CHT-SO$_4$-LA (Run 3) was washed with water. No activity was found in this wash liquid by the Clinistix strip method thus indicating that the enzyme was indeed bound to the immobilized product.

EXAMPLE 2

To 10 g of air-dried chitosan flakes, 30–40 mesh, was added 250 ml of 0.1 M $H_2SO_4$; the mixture was stirred mechanically at 20° C. for 1 hour. The treated flakes were collected by filtration was washed with about 200 ml of distilled water. The product was air-dried (12.9 g).

A 2.0-g portion of this chitosan sulfate was contacted with a mixture containing 10 ml of water plus 0.2 ml of the stock Sucrovert solution for 1 hour with gentle agitation. The mixture was filtered and the solid CHT-$SO_4$-INV was washed with distilled water and then dried in air.

The invertase activity of the product was determined by the aforementioned Glucostat procedure and found to be 98 micromoles of glucose per minute per g of CHT-$SO_4$-INV.

EXAMPLE 3

Run 1: To 300 g of air-dried chitosan, 30–40 mesh, was added a mixture of 150 ml of 25% aqueous glutaraldehyde and 1200 ml of water. The mixture was stirred for 1 hour at 20° C. The solid was collected by filtration, washed with about 5 l of water, 1 l of methanol, and about 300 ml of ethyl ether, and air-dried to give 342 of chitosan cross-linked with glutaraldehyde. The cross-linked chitosan contained 6.56% nitrogen compared to a corresponding value of 7.37% nitrogen for the starting chitosan.

A 5 g portion of the chitosan-glutaraldehyde product was suspended in 100 ml of 0.2 M sodium acetate buffer (pH 5.0) at 20° C. To this suspension was added 1 ml of the stock Sucrovert solution. The product (CHT-GA-INV) was washed thoroughly with water, with about 100 ml of saturated potassium chloride, with about 100 ml of 0.2 M acetate buffer at pH 5.0, and then with about 500 ml of distilled water. The product was dried in air (5.13 g).

Run 2: The procedure described above for Run 1 was followed with the exception that crude lactase (0.5 g) was substituted for the stock Sucrovert solution. The air-dried product weighed 5.44 g.

The activities of the product are set forth in the table below.

| Run | Insolubilized enzyme | Activity Micromoles of glucose produced per minute per g of insolubilized enzyme |
|---|---|---|
| 1 | CHT-GA-INV | 183 |
| 2 | CHT-GA-LA | 262 |

Having thus described our invention, we claim:

1. A process for preparing an insoluble but active enzyme, which comprises
   (a) dissolving a soluble active enzyme in water,
   (b) dissolving chitosan in water at pH 3–7,
   (c) mixing the aqueous solution of the enzyme with the solution of chitosan, and
   (d) precipitating an insoluble but active enzyme from the mixture by addition thereto of an agent selected from the group consisting of alkaline agents and sources of sulfate ions.

2. The process of claim 1 wherein the enzyme and chitosan are simultaneously dissolved in water at pH 3–7.

3. The process of claim 1 wherein the enzyme is a sugar-hydrolyzing enzyme.

4. The process of claim 1 wherein the enzyme is invertase.

5. The process of claim 1 wherein the enzyme is a glucose-oxidizing enzyme.

6. A process for preparing an insoluble but active enzyme, which comprises
   (a) dissolving a soluble active enzyme in water,
   (b) treating chitosan to form chitosan sulfate by a method selected from the group consisting of
      (1) dividing solid chitosan into small pieces of about 10–60 mesh and contacting the pieces with sulfuric acid and
      (2) dissolving chitosan in water at pH 3–7 and adding thereto a source of sulfate ions, and
   (c) contacting the chitosan sulfate with the aqueous solution of the enzyme to produce an insoluble but active enzyme.

7. The process of claim 6 wherein the enzyme is a sugar-hydrolyzing enzyme.

8. The process of claim 6 wherein the enzyme is invertase.

9. The process of claim 6 wherein the enzyme is a glucose-oxidizing enzyme.

* * * * *